(12) United States Patent
Al Qahtani

(10) Patent No.: US 11,523,928 B2
(45) Date of Patent: Dec. 13, 2022

(54) CHOANAL ATRESIA APPARATUS

(71) Applicant: National Establishment for Medical Supplies, Abha (SA)

(72) Inventor: Ali Saeed Mohammed Al Qahtani, Abha (SA)

(73) Assignee: College of Medicine of King Khalid University, Abha (SA)

( * ) Notice: Subject to any disclaimer, the term of this patent is extended or adjusted under 35 U.S.C. 154(b) by 965 days.

(21) Appl. No.: 16/258,062

(22) Filed: Jan. 25, 2019

(65) Prior Publication Data

US 2020/0237548 A1 Jul. 30, 2020

(51) Int. Cl.
*A61F 2/18* (2006.01)
*A61F 5/08* (2006.01)
*A61F 11/20* (2022.01)

(52) U.S. Cl.
CPC ............... *A61F 5/08* (2013.01); *A61F 2/186* (2013.01); *A61F 11/20* (2022.01)

(58) Field of Classification Search
CPC .. A61F 5/08; A61F 2/186; A61F 11/20; A61F 11/202; A61F 2/04; A61F 2002/072; A61F 2002/828; A61F 2/852; A61F 2230/0006; A61F 2250/0018; A61F 2250/0039; A61F 2250/0062
USPC ...................................................... 623/1.27
See application file for complete search history.

(56) References Cited

U.S. PATENT DOCUMENTS

| | | | | |
|---|---|---|---|---|
| 3,814,103 A | * | 6/1974 | Fettel ................ | A61M 16/0666 128/207.18 |
| 3,867,946 A | * | 2/1975 | Huddy .............. | A61M 16/0666 128/207.18 |
| 4,850,999 A | * | 7/1989 | Planck ............... | A61F 2/06 623/1.32 |
| 6,606,995 B1 | * | 8/2003 | Sadek ............... | A61F 5/08 128/207.14 |
| 8,974,486 B2 | * | 3/2015 | Kotler ............... | A61F 5/08 128/207.14 |
| 2003/0153937 A1 | * | 8/2003 | Al-Qahtani .......... | A61F 11/202 606/162 |
| 2004/0087885 A1 | * | 5/2004 | Kawano ............. | A61M 25/0043 604/524 |
| 2005/0066976 A1 | * | 3/2005 | Wondka ............. | A61M 16/0605 128/207.18 |

(Continued)

FOREIGN PATENT DOCUMENTS

WO WO-2020152508 A1 * 7/2020 ............. A61F 2/186

OTHER PUBLICATIONS

International Preliminary Examination Report of WO2020152508 published Jul. 2020 (Year: 2020).*

*Primary Examiner* — Paul B Prebilic

(74) *Attorney, Agent, or Firm* — Lewellyn Law, PLLC; Stephen Lewellyn

(57) ABSTRACT

A choanal atresia apparatus for use in prevention of stenosis following choanal atresia repair in patients. Two tubular choanal tubes each have an interior surface and an exterior surface, an anterior end and a posterior end, and a central axis. A plurality of axially spaced apertures in each of the two choanal tubes are for discharging nasal secretion. A strip has opposed ends coupled to the posterior ends of the two choanal tubes respectively. The strip couples the two choanal tubes in a laterally spaced relationship. The choanal tubes and the strip are fabricated of a medical grade plastic.

7 Claims, 3 Drawing Sheets

(56) References Cited

U.S. PATENT DOCUMENTS

2006/0085027 A1* 4/2006 Santin ................. A61F 5/56
606/199
2019/0358078 A1* 11/2019 Akihiro ............... A61F 5/08
2020/0237548 A1* 7/2020 Al Qahtani ........... A61F 2/186

* cited by examiner

CHOANAL ATRESIA APPARATUS

BACKGROUND OF THE INVENTION

Field of the Invention

This invention relates to an apparatus for use in the treatment of choanal atresia, especially for the prevention of stenosis following choanal atresia repair.

Choanal atresia, obstruction of the posterior nasal openings, is the most common congenital nasal anomaly of newborn infants with an incident of approximately 1 in 5000 to 7000 live births which necessitates urgent medical intervention. A newly born infant is an obligatory nose breather. Mouth-breathing is a learned reflex that can take from hours to days to acquire. Until opening of the mouth is learned, cyclical respiratory obstructions can occur. As a child falls asleep, his/her mouth closes, and a progressive obstruction can result, starting with a stridor and progressing to increased effort and cyanosis. Normally the initial alerting event is the first feeding of a newborn infant. As the child startles, a progressive obstruction of the airway occurs with cyanosis and hypoxia to the point of aspiration of milk and choking. Accordingly, a newborn infant can fail to thrive.

This congenital condition is normally treated by surgical opening of the choanae using a drill, an endoscope, or a laser. Whereas such treatments provide immediate relief, surgically formed openings tend to re-close. Additionally, the same conditions can be acquired in adults via various circumstances including post-radiation of head and neck tumors. To this extent ear, nose and throat (ENT) surgeons differ widely on how to prevent restenosis of the formed openings. Some surgeons place stents fashioned from several hard and soft materials in the formed openings. Most common of these is a stent made by modifying an endotracheal tube. Such a stent is disclosed in UK-A-2352976. Other surgeons prefer to perform serial dilatation of the openings once a week for 4-6 weeks. Still others maintain patency by regular bougienage every two months. All of these procedures are time consuming and none is entirely satisfactory.

Applicant believes that a cause of failure of stents produced by modifying endotracheal tubes is related to the material from which the stents are produced and structure of how they are made. Tracheal tubes are generally produced from polyvinyl chloride which softens at body temperature and can consequently collapse under an attempt at re-epithelialization of choanae. In addition, repeated anesthetics unnecessarily subject newborn infants to the hazards of multiple anesthetics and tracheal intubation. Also, stents made of rubber may induce localized toxic tissue reaction.

One object of this invention is to provide apparatus for use in the treatment of choanal atresia which does not suffer from, or at least alleviates, the disadvantages discussed above.

SUMMARY OF THE INVENTION

According to the present invention, there is provided an apparatus for use in the prevention of stenosis following choanal atresia repair in infants. The apparatus comprises two choanal tubes adapted to lie side-by-side. Each is of a plastics material approved for use in humans and each has a lengthwise extending flexible metallic insert embedded internally within its wall. A strip of plastics material has ends attached one to one end of each of the choanal tubes. A bridge of plastics material extends between and is removably attached to the choanal tubes at or towards their ends remote from the strip of plastics material. The arrangement is such that, in use, the choanal tubes are positioned in the nasal passageways and transnasal openings of an infant with the plastics strip extending behind the cartilage which separates the nasal passageways, and with the bridge positioned adjacent to the columella of the nose.

Each metallic insert may comprise a spiral of metallic material embedded within the respective choanal tube. The metallic material may be stainless steel. In a preferred embodiment of the invention, each metallic insert comprises a stainless steel wire coil embedded internally within the respective choanal tube.

A plurality of axially spaced apertures are formed in each of the two choanal tubes for discharging nasal secretion. Each choanal tube may be produced from silicone rubber or polyvinyl chloride.

Each metallic insert may extend over the major part of the length of the respective choanal tube.

The ends of the plastics strip may be permanently or releasably attached to the ends of the choanal tubes.

The bridge may be held in place by a thread which passes through apertures formed in the choanal tubes.

A piece of resilient material may be attached to that side of the bridge opposite the plastics strip. The resilient material may be produced from a sponge-like material.

The diameter of each choanal tube preferably lies in the range 2.5 to 8.0 mm.

In another aspect, the invention provides apparatus for use in the treatment of choanal atresia which comprises two side-by-side choanal tubes each of a material approved for use in humans and each reinforced with an embedded lengthwise extending filament coil, and a strip of material approved for use in humans whose ends are attached to one end of each tube.

The material of the choanal tubes and the strip may be plastics, for example polyvinylchloride.

A bridge of plastics material may be releasably secured to each choanal tube at positions at or towards the ends of the tubes remote from the strip of plastics material.

The embedded filament coil may comprise a spiral of metallic material, for example stainless steel.

The plastics strip may be permanently or separably attached to the ends of the two choanal tubes.

BRIEF DESCRIPTION OF THE DRAWINGS

A specific embodiment of the invention will now be described by way of example with reference to the accompanying diagrammatic drawings in which.

The same reference numerals refer to the same parts throughout the various Figures.

DESCRIPTION OF THE PREFERRED EMBODIMENT

Figures 1, 2:
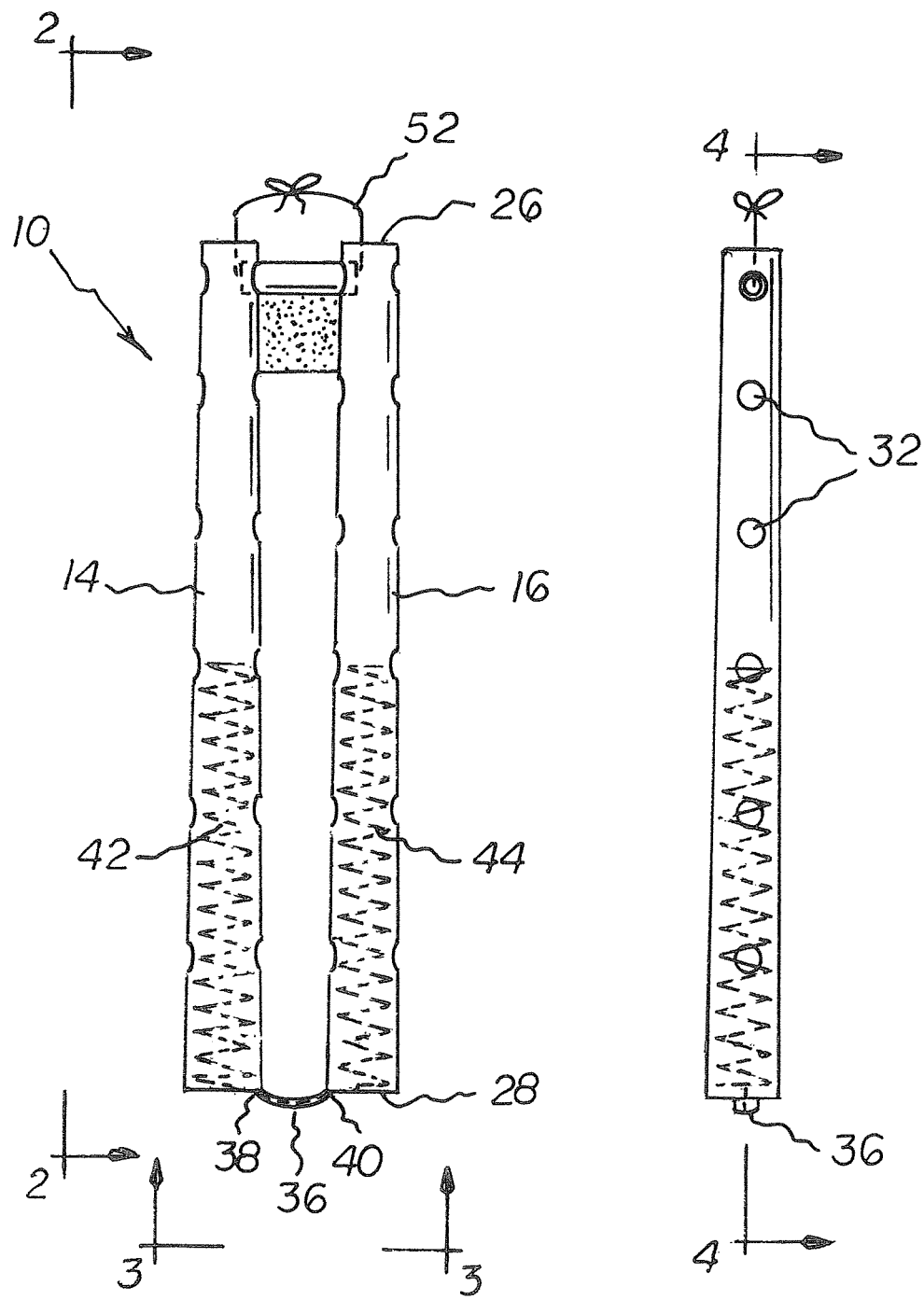
FIG. 1 is a front elevational view of a choanal atresia apparatus constructed in accordance with the principles of the present invention.
FIG. 2 is a side elevational view taken along line 2-2 of FIG. 1.
Figure 3:
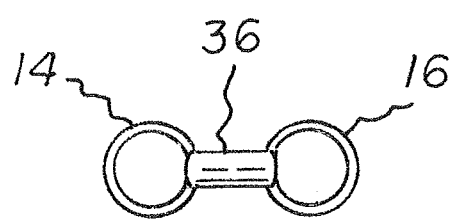
FIG. 3 is a bottom view taken along line 3-3 of FIG. 1.
Figure 4:
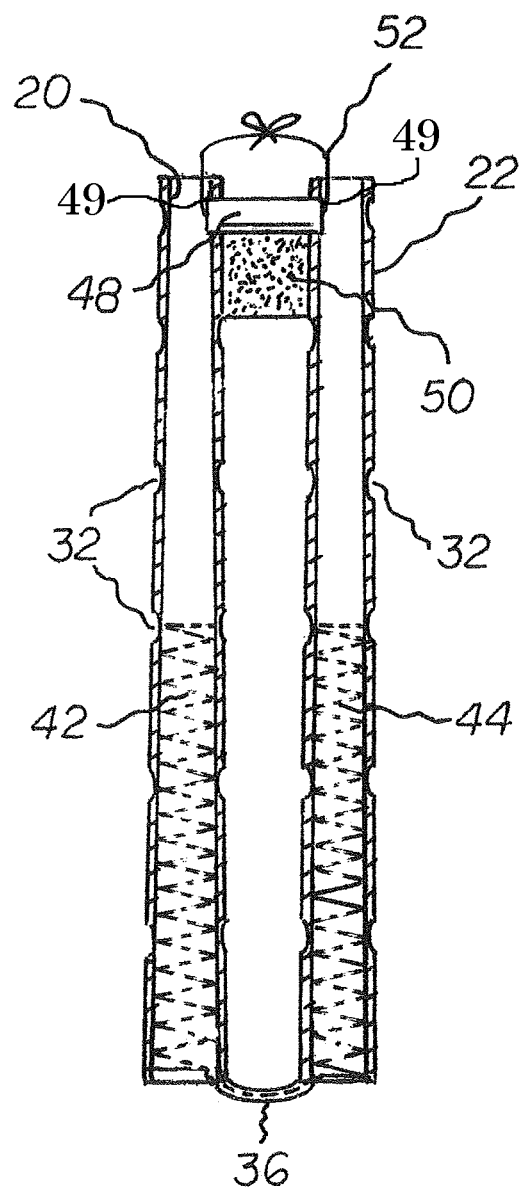
FIG. 4 is a cross sectional view taken along line 4-4 of FIG. 2.
Figure 5:
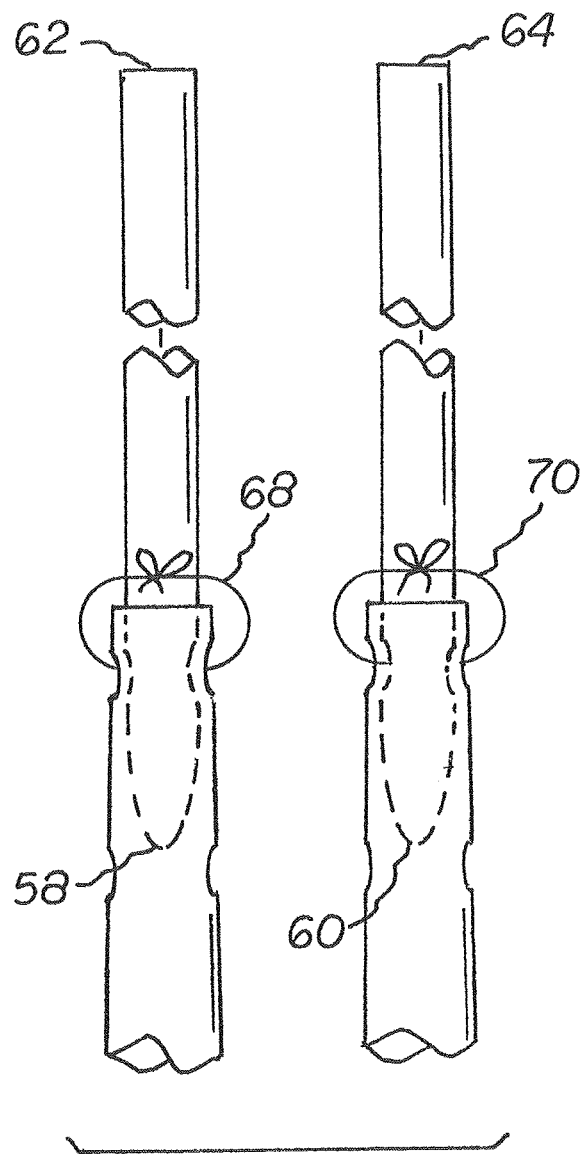
FIG. 5 is a front elevational view of the choanal atresia apparatus and the distal ends of the catheters after coupling.
Figure 6:
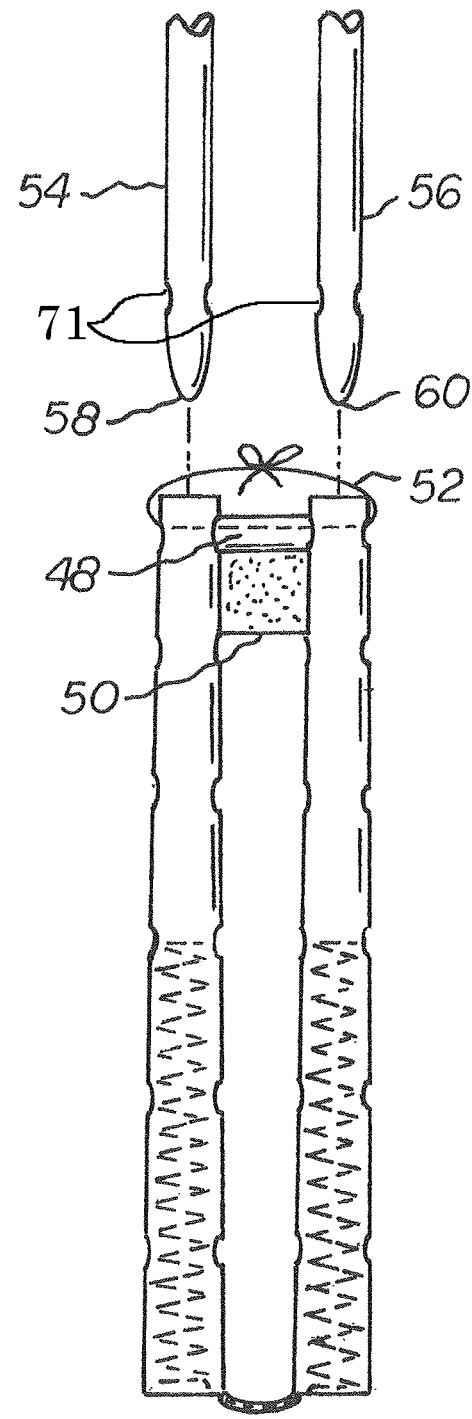
FIG. 6 is a front elevational view of the choanal atresia apparatus and the distal ends of the catheters after separation.

With reference now to the drawings, and in particular to FIG. 1 thereof, the preferred embodiment of the new and improved choanal atresia apparatus embodying the principles and concepts of the present invention and generally designated by the reference numeral 10 will be described.

The present invention, the choanal atresia apparatus 10 is comprised of a plurality of components. Such components in their broadest context include a two choanal tubes with apertures therein and a plastic strip. Such components are individually configured and correlated with respect to each other so as to attain the desired objective.

The choanal atresia apparatus 10 of the present invention is for use in prevention of stenosis following choanal atresia repair in patients. In the preferred embodiment, two choanal tubes 14, 16 are first provided. Each of the two choanal tubes is tubular in configuration with an interior surface 20 and an exterior surface 22, an anterior end 26 and a posterior end 28, and a central axis. The two choanal tubes are fabricated of a medical grade plastic. Each choanal tube has an anterior part with an interior anterior diameter. Each choanal tube also has a posterior part with an interior posterior diameter. The internal diameter of the anterior part of each choanal tube is less than the interior diameter of the posterior part of each choanal tube by 0.3 to 0.5 millimeters to thereby create a cone shape for each choanal tube. Each choanal tube has an exterior diameter of from 2.5 millimeters to 8.0 millimeters for the purpose of fitting into the various sizes of nasal passages based on the age of the patient. The entire length of each choanal tube is 7.5 centimeters plus or minus 20 percent.

Next provided are a plurality of axially spaced apertures 32 in each of the two choanal tubes for discharging nasal secretion. The plurality of axial spaced apertures includes five apertures on each side of each choanal tube. The five apertures are spaced equidistant to each other by 1 centimeter, plus or minus 20 percent. The five apertures are punched through the choanal tubes so as to create a full pass. The apertures start 1.50 centimeter, plus or minus 20 percent, from the anterior end and continue posteriorly at 1.00 centimeter, plus or minus 20 percent, intervals. The diameter of each aperture is from 1 to 2 millimeters.

A strip 36 is next provided. The strip has opposed ends 38, 40 coupled to the posterior ends of the two choanal tubes respectively. The strip couples the two choanal tubes in a laterally spaced relationship. The strip secures the two choanal tubes laterally spaced by a distance of from 0.5 centimeters to 1.0 centimeters for resting upon septal cartilage between the nasal passageways of a patient. The strip is fabricated of a medical grade plastic.

Next, two flexible inserts 42, 44 are provided. Each of the flexible inserts is embedded within the interior surface of an associated choanal tube. The two flexible inserts are fabricated of a metallic material in a coil spring configuration. The two flexible inserts extend from the middle of the choanal tubes, 3.75 centimeters, plus or minus 20 percent, from the anterior end, and continuing posteriorly. The two flexible inserts are in a vortex type manner. Each flexible insert covers the posterior half only of each tube.

A bridge 48 is next provided. The bridge is formed as a tube of polyvinyl chloride positioned at the anterior end of the choanal tubes. Particularly, opposite ends of the bridge are removably received in cooperating bridge holes 49 formed through the choanal tubes at the anterior ends thereof. A spacer 50 is positioned adjacent to the bridge and is formed in a generally cubical configuration measuring 3 to 5 millimeters long by 2 to 3 millimeters wide by 3 to 5 millimeters deep. The spacer is fabricated of a soft sponge-like silicone or equivalent soft material. The spacer is coupled to the choanal tubes adjacent to the bridge via a safe adhesive. A single tie 52 is provided at the proximal ends of the choanal tubes. The tie extends through the bridge.

Lastly, two catheters 54, 56 are provided. Each catheter has a distal end 58, 60 and a proximal end 62, 64. Two ties 68, 70 couple the distal ends of the catheters to the anterior ends of the two choanal tubes respectively. The two catheters when pulled function together to pull the two choanal tubes in position within the nasal passageways.

In using the apparatus of the present invention, a first catheter 54 is inserted into a first nasal passageway of a patient, and a second catheter 56 is inserted into a second nasal passageway of the patient. The insertions involve pushing the distal ends 58, 60 of the catheters into the anterior ends of the nasal passageways. The pushing continues until the distal ends of the catheter extend through the nasopharynx to the oropharynx and then to the mouth of the patient with the proximal ends of the catheters outside of the nasal passageways of the patient.

The anterior ends of the choanal tubes are then coupled to the distal ends of the catheter with ties 68, 70 that are passed through catheter holes 71 that extend laterally through the catheters at the distal ends thereof. The proximal ends 62, 64 of the catheter are then pulled anteriorly through the nasal passageways until the strip between the choanal tubes rests upon septal cartilage between the nasal passageways. The anterior ends of the choanal tubes are then uncoupled from the distal ends of the catheters with the choanal tubes in place. Lastly, a tubular bridge and a spacer and a tie are coupled to the anterior ends of the choanal tubes for proper position during use of the choanal tubes with respect to the nasal passageways of the patient.

The present invention is an apparatus for use in the treatment of choanal atresia and in the prevention of stenosis following choanal atresia repair in patients, including infants. The apparatus comprises two choanal tubes adapted to lie side-by-side, each fabricated of a plastics material approved for use in humans. Each choanal tube has a lengthwise extending flexible metallic insert embedded internally within its interior surface.

A strip of plastic has ends attached one to one end of each of the choanal tubes. A bridge of plastics material extends between and is removably attached to the choanal tubes at or towards their ends remote from the strip of plastics material. The arrangement is such that, following choanal atresia repair in patients, including infants and adults, the choanal tubes are positioned in the nasal passageways and transnasal openings of a patient with the plastics strip extending behind the sepal cartilage which separates the nasal passageways, and with the bridge positioned adjacent to the columella of the nose.

Multiple apertures are formed at the sides of both the tubes, as when the tube is facing forward for insertion. There will preferably be a total of five apertures on each side spaced equidistant to each other by 1 centimeter. The apertures will be "punched through" the tube, so as to create a full pass. The tube is preferably made of Z79-IT plastic, already approved for use in human medical devices. The entire length of the tube is preferably 7.5 centimeters. The apertures, therefore, will start 1.50 centimeter from the anterior end and continue posteriorly at 1.00 centimeter intervals. The diameter of each aperture is 1 to 2 millimeters. The entire tube diameter will vary from 2.5 millimeters to 8.0 millimeters for the purpose of fitting into the various sizes of nasal passages based on the age of the patient.

The benefit of these apertures is to allow bloody secretion to pass in the nasal cavity following surgery. The secretion can then be cleaned by an attending nurse. It is also conducive for ventilation of mucosa, as insufficient methods are believed to be a major factor predisposing to sinusitis. The ventilation of the paranasal sinuses is critical for the entry aerosols into their cavities.

The internal diameter of the anterior part of tube is less than posterior by 0.3 to 0.5 millimeters. Such is the configuration on both sides of the tube from the anterior to posterior. This will create a "cone shaped" scenario for each tube. The entire size of the tube diameter will vary from 2.5 millimeters to 8.0 millimeters for the purpose of fitting into the various sizes of nasal passages based on the age of the patient. So for example, the tube that is 2.5 millimeters in diameter will be 2.5 millimeters in the posterior and 2.2 to 2.0 millimeters in the anterior.

The benefit of the internal diameter of anterior part of tube being less than posterior by 0.3 to 0.5 millimeters is to avoid pressure on both alar cartilages and columella. This will be helpful in preventing pressure necrosis of columella and alar cartilage. Another benefit of this structure is that it will facilitate the introduction of the choanal tubes through nasal cavity.

Provided next is the strip. The strip, a flexible strand of a metallic material that is totally imbedded in the strip. The strip is an extension of the flexible inserts totally imbedded in the choanal tubes. The strip with the flexible strand functions for the purpose of connecting both tubes. The strip is preferably fabricated of Z79-IT plastic and is 0.5 to 1 centimeter in length. This same metal material is also inserted into both tubes. It is imbedded into the tubes in the manufacturing process and will be inspected for quality and strength.

The benefit of the imbedded metal strand into the strip posteriorly is that it will function as a continuation of the flexible insert metal in both tubes which will secure both tubes strongly. It will also improve their stability in the choana, the posterior opening of the nose, as well as preventing the tube to cause pressure on the posterior part of nasal septum and vomer.

The bridge, preferably a tube of polyvinyl chloride, is positioned at the anterior portion of the choanal tubes. Adjacent to the bridge is a spacer in a generally cubical configuration measuring 3 to 5 millimeters long by 2 to 3 millimeters wide by 3 to 5 millimeters deep. The spacer is a piece of silicone, or equivalently soft sponge-like material. The spacer is coupled to the choanal tubes adjacent to the bridge via gorilla glue or equivalent safe adhesive.

The proximal ends of the choanal tubes are fixed with a tie of silk or proline or nylon tie through the bridge.

The benefit of this bridge and spacer and tie is that it will be helpful in preventing pressure necrosis of columella in a manner that will be comfortable to the patient.

Provided next are the two flexible inserts. The flexible inserts are fabricated of a metal material in a coil spring configuration that is imbedded in the both sides of the tube. The metal will begin from the middle of the choanal tubes, 3.75 centimeters from the anterior end, and continue all the way to the choana. It will be placed in a vortex type manner so as to create a "swirled" look inside the tubes. The flexible insert will, in the preferred embodiment, cover the posterior half of each tube only. The flexible insert may, in alternate embodiments, cover more or less than half of the length of one of the choanal tubes.

The benefit of the flexible inserts imbedded in the tubes is that it will be helpful in preventing posterior opening, choana, to restenosis and avoid pressure necrosis of anterior half of the nasal cavity when used on the patient.

The apparatus can be used in both infants and adults, hence the various sizes in the claims.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A choanal atresia apparatus for use in prevention of stenosis following choanal atresia repair in patients, the apparatus comprising, in combination:
   two choanal tubes, each choanal tube having an anterior end, a posterior end, a length extending therebetween, a passage extending the entire length, and a plurality of secretion holes spaced along the length and connecting an exterior of the tube with the passage, the secretion holes allowing nasal secretion to pass into the passage;
   a strip coupling the posterior ends of the choanal tubes in a laterally spaced relationship;
   a bridge connected to and extending between the anterior ends of the choanal tubes, opposite ends of the bridge being removably received in cooperating bridge holes formed through the choanal tubes at the anterior ends thereof;
   a first tie threaded through the bridge holes and the bridge and having opposite ends tied together at a position exteriorly of the choanal tubes;
   a spacer disposed posteriorly of the bridge and extending between the choanal tubes;
   first and second catheters, each catheter having a distal end and a catheter hole extending laterally through the catheter at the distal end thereof;
   a second tie removably coupling the distal end of the first catheter to the anterior end of one choanal tube with the second tie threaded through the catheter hole of the first catheter and a pair of secretions holes that are disposed on opposite sides of the one choanal tube;
   a third tie removably coupling the distal end of the second catheter to the anterior end of a second choanal tube with the third tie threaded through the catheter hole of the second catheter and a pair of secretion holes that are disposed on opposite sides of the second choanal tube; and
   wherein when the first and second catheters are coupled to the choanal tubes, the catheters when pulled in an anterior direction pull the choanal tubes in position within the nasal passageways of a patient when the choanal tubes are inserted into the nasal passageways of the patient.

2. The choanal atresia apparatus of claim 1, wherein:
each choanal tube further includes a flexible insert embedded in the sidewall thereof and extending along a portion of the length.

3. The choanal atresia apparatus of claim 2, wherein the flexible insert of each choanal tube extends along only the posterior half of each choanal tube.

4. The choanal atresia apparatus of claim 2, wherein each flexible insert is a metallic material in a coil spring configuration.

5. The choanal atresia apparatus of claim 1, wherein the strip secures the two choanal tubes laterally spaced by a distance of from 0.5 centimeters to 1.0 centimeters for resting upon septal cartilage between the nasal passageways of a patient.

6. The choanal atresia apparatus of claim 1, wherein the bridge is formed of polyvinyl chloride.

7. The choanal atresia apparatus of claim 1, wherein the two choanal tubes are formed of a medical grade plastic.

* * * * *